United States Patent [19]

Kawashima et al.

[11] Patent Number: 4,496,547
[45] Date of Patent: Jan. 29, 1985

[54] SACCHARIDE FATTY ACID ESTER FOR BLOAT-PREVENTION OR BLOAT-TREATMENT

[75] Inventors: Ryoji Kawashima, Kyoto; Akira Usagawa, Ishikawa; Takayoshi Masuda, Aichi, all of Japan

[73] Assignee: Mitsui Toatsu Chemicals, Inc., Tokyo, Japan

[21] Appl. No.: 451,396

[22] Filed: Dec. 20, 1982

[30] Foreign Application Priority Data

Dec. 25, 1981 [JP] Japan ................ 56-209198

[51] Int. Cl.$^3$ ............ A61K 31/70; A61K 31/72; C07H 13/06
[52] U.S. Cl. .......................... 514/25; 536/115
[58] Field of Search ............ 424/180; 536/119, 115

[56] References Cited

U.S. PATENT DOCUMENTS

| | | | |
|---|---|---|---|
| 2,893,990 | 7/1959 | Hass et al. | 536/119 |
| 3,480,616 | 11/1969 | Osipow et al. | 536/119 |
| 3,714,144 | 1/1973 | Feuge et al. | 536/119 |
| 3,996,206 | 12/1976 | Parker et al. | 536/119 |
| 4,123,522 | 10/1978 | O'Connor et al. | 424/116 |
| 4,327,183 | 4/1982 | Masuda et al. | 536/119 |
| 4,377,686 | 3/1983 | Feuge et al. | 536/119 |

Primary Examiner—Johnnie R. Brown
Attorney, Agent, or Firm—Browdy and Neimark

[57] ABSTRACT

An agent for bloat-prevention or -treatment which is useful for preventing or treating bloat caused by feeding large quantities of legume pasture or concentrate feed to ruminants comprises a mixture of a saccharide fatty acid ester and fatty acid salt.

13 Claims, No Drawings

SACCHARIDE FATTY ACID ESTER FOR BLOAT-PREVENTION OR BLOAT-TREATMENT

BACKGROUND OF THE INVENTION

The present invention relates to an agent for bloat-prevention or -treatment. Further, the present invention relates to an agent for bloat-prevention or -treatment which comprises at least a saccharide fatty acid ester and fatty acid salt.

Bloat is a disease wherein the rumen and a reticulum of a ruminant, for example, cattle, sheep etc. distend severely due to the fermentative gas accumulating therein. Bloat is one of the most horrible diseases in feeding beef cattle, dairy cattle, sheep etc., because ruminants affected with bloat fall into a state of inappetence resulting in the reduction in growth rate or milk yield and, to cite an extreme case, they are suffocated to death.

Though there have been various theories in relation to the cause of bloat, the established theory is today that the feeding of large quantities of legume pasture, or the feeding of large quantities concentrate feed etc. cause bloat. Namely, it is considered as follows: Much legume pasture being fed, the contents of a rumen become liable to foam owing to the actions of foaming substances, such as saponin, vegetable protein etc., contained in a legume pasture, and a roughage being fed insufficiently and much concentrate feed being fed, an abnormal fermentation in the rumen, the viscosity increase of the liquid contained therein, etc., become liable to occur, so that in both cases the exhaustion of gas by eructation is impeded resulting in the excessive distensions of the rumen and the reticulum.

There are known methods for preventing or treating bloat as follows: (1) a method in which much oil is sprinkled on a pastureland; (2) a method in which the amount of a roughage used together with a concentrate feed is kept proper; (3) a method wherein there is used every time a drinking water or a mineral block to which has been added a defoaming agent, for example, silicone, polypropylene glycol (another name: polyoxypropylene glycol), polyoxypropylene/polyoxyethylene block-copolymer; (4) a treating method in which a stomach catheter or a trocar is used for exhausting gas and (5) a treating method employing the administration of much defoaming agent, for example, silicone, polypropylene glycol, polyoxypropylene/polyoxyethylene block-copolymer, mineral oil, vegetable oil etc. However, these methods have respectively the following disadvantages as follows: Namely, the method (1) requires much labor and is not economical, because of sprinkling oil on a large pastureland, and the method (2) has the problem that this method is inconsistent with the system for fattening beef cattle rapidly by feeding much concentrate feed, said system being employed in Japan etc., and it is difficult to achieve excellent results by this method, and the method (4) requires an expert and attended with a strong possibility of the relapse being repeated so long as the cause of bloat is not removed; and though the methods (3) and (5) can show a considerable good effect, the problem in using most defoaming agents known today is that they cause digenstion disturbance owing to the long continuous administration of a defoaming agent, or owing to the administration of much defoaming agent being done at a time. Accordingly, it is today expected that agents with better efficiencies in defoaming effect, etc. and with an improved safety will be produced.

SUMMARY OF THE INVENTION

In consideration of such circumstances as described above, the present inventors have continued research and attained the facts that a mixture comprising at least saccharide fatty acid ester and fatty acid salt has various effects, such as an excellent defoaming effect, the effect lowering the viscosity of a rumen juice, the effect hightening the pH value of said juice, etc., and is further very safe for the living body, so that such a mixture is suitable as an agent for bloat-prevention or -treatment. The facts described above produced the present invention.

DETAILED DESCRIPTION OF THE INVENTION

The animals intended by the agent for bloat-prevention or -treatment of the present invention are ruminants, such as beef cattle, dairy cattle, young cattle, sheep, goats, etc.

Saccharide fatty acid esters being used for the present invention are the fatty acid esters of saccharides, to give typical examples, arabinose, xylose, ribose, lyxose, ribulose, xylulose, glucose, galactose, talose, mannose, fructose, sorbose, tagatose, psicose, maltose, isomaltose, cellobiose, gentiobiose, trehalose, lactose, sucrose, maltotriose, gentianose, raffinose, stachyose, etc. Monoesters, polyesters, such as diesters, triesters, tetraesters etc. and the mixtures of two or more of them are usable. Monoester have one ester linkage in one molecule of saccharide fatty acid ester; polyesters have two or more ester linkages in one molecule of saccharide fatty acid ester.

Among the saccharide fatty acid esters described above, sucrose fatty acid esters are examples of the saccharide fatty acid esters which are most suitable in the present invention, since they are easily available and also considerably low-priced owing to the industrial mass-productions.

The fatty acids with about 6-24 carbons are usually suitable as the fatty acid part of saccharide fatty acid ester. Both saturated and unsaturated fatty acids are usable. Both fatty acids with a straight carbon chain and fatty acids with a branched carbon chain are usable. Further, fatty acids with one or more of substituents, such as a hydroxyl group, etc., are usable. Fatty acids are not necessarily monobasic acids, and dibasic acids, etc. are also usable.

Further, fatty acids are not restricted to the fatty acids from natural materials, such as oils or fats, etc. Synthetic fatty acids are also usable which are produced by the liquid-phase catalytic oxidations of paraffins, the carbonylations of $\alpha$-olefins (oxo method), the carboxylations of branched olefins (Koch's method) or other methods.

The typical examples of such fatty acids are enumerated as follows: caproic acid, enanthic acid, caprylic acid, pelargonic acid, capric acid, lauric acid, tridecanoic acid, 2-methlyltetradecanoic acid, 5-methyltetradecanoic acid, 2,2-dimethyltetradecanoic acid, myristic acid, palmitic acid, margaric acid, stearic acid, arachic acid, behenic acid, lignoceric acid, oleic acid, elaidic acid, linoleic acid, linolenic acid, ricinoleic acid, arachidonic acid, eicosapentaenoic acid, erucic acid, azelaic acid, sebacic acid, 1,20-eicosamethylenedicarboxylic acid, etc.

The saccharide fatty acid esters described above are not necessarily used respectively alone, and the mixtures of two or more kinds of saccharide fatty acid esters of which the saccharide parts are different or of which the fatty acid parts are different or of which the numbers of the ester linkages are different, are also usable in any mixing ratio.

On the other hand, the other component being used for the present invention is fatty acid salt. The typical examples of fatty acid salts are the salts of various fatty acids described above, enumerated as follows: alkali metal salts, such as lithium salts, sodium salts, potassium salts, etc.; alkaline earth metal salts, such as magnesium salts, calcium salts, barium salts, etc.; various metal salts, such as zinc salts, aluminum salts, iron salts, manganese salts, etc.; ammonium salts; organoamine salts, such as monoethanolamine salts, diethanolamine salts, triethanolamine salts, etc.; basic amino acid salts, such as lysine salts, ornithine salts, arginine salts, histidine salts, hydroxylysine salts, etc., and most of all, alkali metal salts, ammonium salts and basic amino acid salts are most generally used.

As described above in relation to saccharide fatty acid esters, the fatty acid salts described above are respectively usable alone and the mixtures of two or more kinds of fatty acid salts of which the fatty acid parts are different or of which the cation parts are different, are also usable as in the case of using one salt alone.

Such saccharide fatty acid esters and fatty acid salts can be easily produced by known methods, and ones produced by any method are usable in the present invention.

The typical examples of processes for preparing saccharide fatty acid esters are enumerated as follows: (1) saccharide and fatty acid lower-alkyl ester, for example, fatty acid methyl ester, fatty acid ethyl ester, etc. are subjected to the alcoholysis using fatty acid salt, for example, fatty acid sodium salt, fatty acid potassium salt, etc. and a basic catalyst in the presence of water or very safe solvent, for example, propylene glycol, etc.; (2) saccharide and fatty acid methyl ester, fatty acid carbitol ester or fatty acid glyceride (mono-, di- and triglyceride), etc. are subjected to alcoholysis in the presence of fatty acid salt, for example, fatty acid sodium salt, fatty acid potassium salt, etc.; (3) saccharide and fatty acid lower-alkyl ester, or oil or fat (that is, fatty acid triglyceride) are subjected to alcoholysis in the presence of a basic catalyst; (4) saccharide is reacted with fatty acid chloride or fatty acid anhydride.

Among these processes, (1), (2) and (3) are very advantageous, because the crude products prepared by these processes contain saccharide fatty acid ester and fatty acid salt (usually, fatty acid alkali metal salt) and can be economically produced and are usable in the present invention without purification, namely, as they are.

On the other hand, fatty acid salts can be easily produced by reacting fatty acid or fatty acid ester, for example, fatty acid methyl ester, fatty acid ethyl ester, fatty acid glyceride, etc. with oxide, hydroxide, carbonate or hydrogen carbonate of alkali metal or alkaline earth metal, etc., basic amino acid, ammonia or organoamine, etc., or by other methods.

The fatty acid salts produced in advance by the above-described methods, etc. are not necessarily used. For example, it is employable to treat as follows: fatty acid and oxide, hydroxide, carbonate or hydrogen carbonate of alkali metal or basic amino acid, etc. are used in the free state each so that fatty acid salt will be prepared in the agent for bloat-prevention or -treatment of the present invention. Employing such methods is within the spirit and scope of the present invention claimed.

The suitable use amount ratio by weight of saccharide fatty acid ester to fatty acid salt in the agent for bloat-prevention or -treatment of the present invention is usually approximately in the range of 97:3 to 3:97, preferably 95:5 to 5:95, most preferably 90:10 to 10:90.

In the present invention it is not required necessarily that the saccharide fatty acid esters and the fatty acid salts be purified to a high degree. In the present invention it is permissable to use the saccharide fatty acid esters and the fatty acid salts accompanied by one or more of the substances highly safe for the living body, such as saccharides, fatty acid lower-alkyl esters, fatty acid glycerides (mono-, di- and triglyceride), fatty acids, alkali metal carbonates, basic amino acids etc. which remain owing to partial unreaction or may remain in the production of saccharide fatty acid ester or fatty acid salt as in the case of the crude saccharide fatty acid ester described above, and byproducts, such as alcohol, glycerin, etc.

The agent for bloat-prevention or -treatment of the present invention is usable in optional forms, such as powder, granule, pellet, crumble, cube, tablet, half-wetted, paste, aqueous solution, aqueous suspension, etc.

The various forms described above being prepared, the following materials may be used as a diluting agent: water; wheat flour, starch, dextrin; feed materials being widely used, for example, cereal grains, such as corn, milo (kaoliang), etc.; chaffs and brans, such as rice bran, deoiled rice-bran, wheat bran, etc.; oil seed meals, such as soybean meal, rape seed meal, cotton seed meal, linseed meal, etc.; oils or fats, such as beef tallow, soybean oil, palm oil, coconut oil, fish oil, etc.

When the agent for bloat-prevention or -treatment of the present invention is administered into animals, the agent for bloat-prevention or -treatment with a form described above is administered apart from a drinking water and a feed, or may be compulsorily injected into a rumen, and however, is most conveniently added into a drinking water or added into a feed to be given to animals. In the feeding system using principally a pasture grass, the present agent may be sprinkled on pasture grasses.

Though the use amount of the agent for bloat-prevention or -treatment of the present invention can not be uniformly fixed because of varying with the factors, such as the kinds, the ages, the body weights, etc. of intended animals, the proper use of the present agent, namely, as an agent for prevention or as an agent for treatment, administration methods, the extent of bloat, the kinds of feeds, etc., the total use amount of saccharide fatty acid ester and fatty acid salt is usually, when being added into a drinking water or a feed to be given to animals, approximately 0.005–10% by weight, preferably 0.01–5% by weight, most preferably about 0.02–3% by weight to the amount of the drinking water or the feed (each containing ingredients other than saccharide fatty acid ester and fatty acid salt) being finally given to animals. In the case that the use amounts described above are less than the lowest limit values, it becomes difficult to show sufficiently the effect of the present invention, and the uses of the amounts exceeding the highest limit values described above do not show any specific effect and are rather uneconomical, so that such uses are not desirable. Using the present agent as an agent for prevention can show a sufficient effect by a continuous administration even if in a relatively low concentration, and using the present agent as an agent for treatment can show the effect of the present invention in a short period by employing a higher concentration than in using the present agent as an agent for prevention.

The agent for bloat-prevention or -treatment of the present invention is usually used alone and can be naturally used together with a known defoaming agent, for example, silicone, polypropylene glycol, polyoxypropylene/polyoxyethylene block-copolymer, oil or fat, etc. or other agents.

Having a much more excellent defoaming effect than conventional agents, the agent for bloat-prevention or -treatment of the present invention can prevent the foaming of the rumen juice of a ruminant and can change a foamed rumen juice into a normal rumen juice. Describing in passing, saccharide fatty acid ester and fatty acid salt have respectively a considerable good defoaming effect (proviso: when saccharide fatty acid ester is not used in rich amount, the defoaming effect is insufficient). However, the combination use of the both can show a very excellent defoaming effect owing to the synergism. The defoaming effect can be more heightened by using saccharide fatty acid ester and fatty acid salt together with fatty acid glyceride, for example, oil or fat (namely, fatty acid triglyceride), fatty acid monoglyceride, fatty acid diglyceride etc. or propylene glycol fatty acid ester, etc.

And, the agent for bloat-prevention or -treatment of the present invention shows the effect which facilitates exhausting immediately the gas produced in a rumen out of the body, because of the effect lowering a stable ingesta volume increase value which is used as a criterion for examining how hard or easy the exhaustion of the fermentative gas produced in a rumen is (the lowering of said value means that the exhaustion of the gas becomes easy), or because of the effect lowering the viscosity of a rumen juice.

Further, the agent for bloat-prevention or -treatment of the present invention has the effect raising the pH value of a rumen juice to the desired degree. The pH value of the rumen juice of a healthy ruminant is usually about 6.5–7.5. However, when much concentrate feed has been fed or when bloat has been induced by an abnormal fermentation, etc. in a rumen, it is frequently observed that the pH value is liable to be lowered (there are various types of bloats, so that certain bloats show the almost same pH value as in a healthy state) and it is not seldom that the pH value lowers down to a pH value of about 4–5. Further, the extreme lowering of the pH value of a rumen juice is a serious problem, because such a extremely-lowered pH value is apt to kill microorganisms in a rumen, such as bacteria, protozoa, etc.

The agent of the present invention shows the effect raising the pH value of a rumen juice to the desired degree by which the environment suitable for the microorganisms in a rumen is kept or recovered, and shows the effect for preventing or treating bloat together with the defoaming effect, etc. described above.

Furthermore, the agent for bloat-prevention or -treatment of the present invention is very safe for the living body and is also easily metabolized in the living body. Therefore, a long continuous administration into an animal and administration of much amount being done at a time do not become a problem in point of safety at all.

As described above, the agent for bloat-prevention or -treatment of the present invention has various effects, such as an excellent defoaming effect, the effect lowering the viscosity of the rumen juice of a ruminant, the effect raising the pH value to the desired degree etc. and has an excellent safety, and therefore has a high practical value as an agent for bloat-prevention or -treatment.

Furthermore, the present invention is in detail explained by means of examples, controls and references hereinafter.

EXAMPLES 1–14

In order to examine artificially the administration effect especially the defoaming effect, of the agent for bloat-prevention or -treatment of the present invention on bloat being frequently induced by the feeding of much leguminous pasture, the various agents for bloat-prevention or -treatment of the present invention comprising respectively at least saccharide fatty acid ester and fatty acid salt, shown in Table 1, were respectively added into an aqueous saponin solution of 0.25% by weight so as to become the respective specified concentration (shown in Table 1) in the resulting solution and the foamabilities of the resulted solutions were determined (proviso: in each case of examples 11–14, the crude products prepared by reaction and containing fatty acid glyceride, sucrose, glycerin, etc. besides saccharide fatty acid ester and fatty acid salt, was added and examined). The results are shown in Table 1. The method for measuring the foamability is shown as follows:

METHOD FOR MEASURING A FOAMABILITY

The agent for bloat-prevention or -treatment of the present invention is added into an aqueous solution of 0.25% by weight in each specified amount and mixed. Just and five minutes after the foaming treatment at 25° C. or 40° C. according to Ross & Miles's method (Japanese Industrial Standard JIS K 3362), the resulted foam height (mm) is measured.

CONTROLS 1 AND 2

The foamability of only the aqueous saponin solution of 0.25% by weight with no agent for bloat-prevention or -treatment of the present invention was measured in each control in the same manner as used in examples 1–14 (the measurement temperature: 25° C. in control 1; 40° C. in control 2). The results were shown in Table 1.

CONTROL 3

Only saccharide fatty acid ester was added into an aqueous saponin solution of 0.25% by weight and the foamability of the resulted solution was measured in the same manner as used in examples 1–14 (the measurement temperature: 25° C.). The results were shown in Table 1.

CONTROL 4

Only fatty acid salt was added into an aqueous saponin solution of 0.25% by weight and the foamability of the resulted solution was measured in the same manner as used in examples 1–14 (the measurement temperature: 25° C.). The results were shown in Table 1.

TABLE 1

The composition and the use amount of the agent for bloat-prevention or -treatment of the present invention

| Example or Control | Saccharide fatty acid ester Kind | Conc. (% by weight) (Note 1) | Fatty acid salt Kind | Conc. (% by weight) (Note 2) | Measurement temperature (°C.) | Foamability (mm) Just after | Foamability (mm) Five minutes after |
|---|---|---|---|---|---|---|---|
| Example 1 | Sucrose hydrogenated beef tallow fatty acid ester (mono-: 70% by w. / di-: 30% by w.) | 0.20 | Stearic acid potassium salt | 0.05 | 25 | 23 | 20 |
| Example 2 | Sucrose hydrogenated beef tallow fatty acid ester (mono-: 70% by w. / di-: 30% by w.) | 0.20 | Stearic acid potassium salt | 0.05 | 40 | 22 | 19 |
| Example 3 | Sucrose hydrogenated beef tallow fatty acid ester (mono-: 70% by w. / di-: 30% by w.) | 0.05 | Stearic acid potassium salt | 0.20 | 25 | 23 | 21 |
| Example 4 | Sucrose hydrogenated beef tallow fatty acid ester (mono-: 70% by w. / di-: 30% by w.) | 0.05 | Stearic acid potassium salt | 0.20 | 40 | 24 | 22 |
| Example 5 | Sucrose hydrogenated beef tallow fatty acid ester (mono-: 70% by w. / di-: 30% by w.) | 0.033 | Stearic acid potassium salt | 0.017 | 25 | 21 | 18 |
| Example 6 | Sucrose hydrogenated beef tallow fatty acid ester (mono-: 70% by w. / di-: 30% by w.) | 0.017 | Stearic acid potassium salt | 0.033 | 25 | 23 | 20 |
| Example 7 | Sucrose hydrogenated beef tallow fatty acid ester (mono-: 70% by w. / di-: 30% by w.) | 0.20 | Coconut fatty acid sodium salt | 0.05 | 25 | 16 | 12 |
| Example 8 | Sucrose beef tallow fatty acid ester (mono-: 65% by w / di-: 30% by w. / tri-: 5% by w.) | 0.05 | Palmitic acid L-lysin salt | 0.05 | 25 | 25 | 20 |
| Example 9 | Raffinose beef tallow fatty acid ester (mono-: 60% by w. / di-: 30% by w. / tri-: 10% by w.) | 0.15 | Oleic acid sodium salt | 0.10 | 40 | 14 | 9 |
| Example 10 | Maltotriose mono-palmitic acid ester | 0.10 | Beef tallow fatty acid sodium salt | 0.05 | 40 | 20 | 15 |
| Example 11 | The crude products prepared (Note 3) by subjecting sucrose and beef tallow to the alcoholysis using potassium carbonate as a catalyst was added so as to become 0.25% by weight. | | | | 25 | 0 | 0 |
| Example 12 | The crude products prepared (Note 3) by subjecting sucrose and beef tallow to the alcoholysis using potassium carbonate as a catalyst was added so as to become 0.25% by weight. | | | | 40 | 0 | 0 |
| Example 13 | The same crude products as used in examples 11 and 12 was added so as to become 0.05% by weight. | | | | 25 | 11 | 0 |
| Example 14 | The same crude products as used in examples 11 and 12 was added so as to become 0.05% by weight. | | | | 40 | 6 | 0 |

TABLE 1-continued

The composition and the use amount of the agent for bloat-prevention or -treatment of the present invention

| Example or Control | Saccharide fatty acid ester | | Fatty acid salt | | Measurement temperature (°C.) | Foamability (mm) | |
|---|---|---|---|---|---|---|---|
| | Kind | Conc. (% by weight) (Note 1) | Kind | Conc. (% by weight) (Note 2) | | Just after | Five minutes after |
| Control 1 | | | | | 25 | 220 | 195 |
| Control 2 | | | | | 40 | 228 | 204 |
| Control 3 | Sucrose hydrogenated beef tallow fatty acid ester (mono-: 70% by w. di-: 30% by w.) | 0.05 | | | 25 | 56 | 45 |
| Control 4 | | | Stearic acid potassium salt | 0.05 | 25 | 212 | 183 |

Notes 1 and 2. The both concentrations mean the concentrations of saccharide fatty acid ester and fatty acid salt in the solution prepared by being added into an aqueous saponin solution of 0.25% by weight (proviso: the concentration of the crude products prepared by reaction was showed in each of examples 11–14).
Note 3. The crude products prepared by reaction, said crude products comprising 30% by weight sucrose beef tallow fatty acid ester (monoester/diester = 65/35 weight ratio), 25% by weight beef tallow fatty acid potassium salt, 20% by weight beef tallow fatty acid glyceride (the total amount of mono-, di- and triglyceride) and 25% by weight others (sucrose, glycerin etc.), was used in examples 11–14.

REFERENCE 1

The commercially available agent for bloat-prevention (polyoxypropylene/polyoxyethylene block-copolymer, the molecular weight: 1250, the content of polyoxyethylene parts: 20%) was added into an aqueous saponin solution of 0.25% by weight so as to become 0.25% by weight in the resulting solution. The foamability of the resulted solution was measured in the same manner as used in examples 1–14 (the measurement temperature: 25° C.). The foamability was 65 mm just after the foaming treatment and 57 mm five minutes after the foaming treatment.

REFERENCE 2

The same commercially available agent for bloat-prevention as used in reference 1 was added into an aqueous saponin solution of 0.25% by weight so as to become 0.05% by weight in the resulting solution. The foamability was measured in the same manner as used in examples 1–14 (the measurement temperature: 25° C.). The foamability was 172 mm just after the foaming treatment and 152 mm five minutes after the treatment.

REFERENCE 3

The commercially available agent for bloat-prevention (polyoxypropylene/polyoxyethylene block-copolymer, the molecular weight: 2000, the content of polyoxyethylene parts: 50%) was added into an aqueous saponin solution of 0.25% by weight so as to become 0.25% by weight in the resulting solution. The foamability of the resulted solution was measured in the same manner as used in examples 1–14 (the measurement temperature: 25° C.). The foamability was 185 mm just after the foaming treatment and 168 mm five minutes after the foaming treatment.

EXAMPLES 15–17

It is shown by the under-described experiment that the fermentative gas is easily exhausted by adding the agent for bloat-prevention or -treatment of the present invention into the rumen juice of a ruminant.

EXPERIMENT METHOD

Rumen juice is collected from three sheep affected with bloat artificially by feeding the bloat-inducing feed (the feed described in "D. R. Jacobson et al., Journal of Animal Science, Vol. 16, pages 515–524 (1957)", said feed comprising 61% barley, 22% alfalfa meal, 16% soybean meal and 1% NaCl), and the mixture of the three rumen juices collected is used as the rumen juice for the present experiment.

Next, 200 ml of said mixture is poured into a 500 ml messcylinder and thereinto the agent for bloat-prevention or -treatment of the present invention is added in each specified amount and thereafter the resulting mixture is incubated at 39° C. for one hour in an incubator and further incubated with stirring by a glass rod every five minutes for one hour and the volume increase rate (%) of the rumen juice in the messcylinder is measured and the value of said rate is used as the stable ingesta volume increase (referred to as Stable IVI hereinafter). Stable IVI teaches that the smaller Stable IVI becomes, the easier exhausting the fermentative gas out of a rumen juice becomes.

EXPERIMENT CONDITIONS AND RESULTS

The experiment conditions and results are shown in Table 2. The agent for bloat-prevention or -treatment of the present invention which was used in the present experiment is the crude products prepared by subjecting sucrose and beef tallow to the alcoholysis using potassium carbonate as a catalyst and said crude products are the same as used in examples 11–14.

CONTROL 5

Stable IVI of only the rumen juice without the agent for bloat-prevention or -treatment of the present invention was measured in the same manner as used in examples 15–17. The result is shown in Table 2.

EXAMPLE 18

Eighteen Holstein bulls of eight weeks of age were divided into three groups respectively consisting of six Holstein bulls and the feeding trials were carried out by feeding the feeds with the respective composition shown in Table 3 to respective group for five weeks (namely, till thirteen weeks of age). Besides the respective feed with the composition shown in Table 3, dried grass was fed as a roughage to bulls of all groups at the rate of about 0.3 kg/bull/day (this amount corresponds to about one-tenth the feeding amount shown in Table 3). During the feed trials, the rumen juices of the bulls of all groups were collected at 10 and 13 weeks of age, and the viscosity and the pH value of each rumen juice were measured. The average viscosity and the average pH value of the bulls per group were calculated and shown in Table 3.

TABLE 2

| Example or Control | Agent for bloat-prevention or -treatment | | Stable IVI (%) |
|---|---|---|---|
| | Kind | Concentration to the rumen juice (% by weight) | |
| Example 15 | The same crude products as used in examples 11-14 | 0.5 | 21 |
| Example 16 | The same crude products as used in examples 11-14 | 1 | 19 |
| Example 17 | The same crude products as used in examples 11-14 | 2 | 20 |
| Control 5 | | | 47 |

TABLE 3

| Group Division | 1 Test No. 1 | 2 Test No. 2 | 3 Control |
|---|---|---|---|
| Ingredients and mixing ratio (parts by weight) in each given feed | | | |
| Commercially available feed for young cattle (Note 1) | 100 | 100 | 100 |
| Agent for bloat-prevention or -treatment of the present invention (Note 2) | 1 | 0.2 | 0 |
| State of each rumen juice | | | |
| Viscosity (cp/25° C.) | 7.7 | 9.5 | 13.5 |
| pH | 7.1 | 6.7 | 6.5 |

Note 1.
DCP (digestible crude protein): 18%
TDN (total amount of digestible nutrients): 68%
Note 2.
The same crude products as used in examples 11-17 was used.

EXAMPLE 19

Ten Holstein bullocks weighing about 450 kg were divided into two groups (test group and control group) respectively consisting of five Holstein bullocks and the feeding trials were carried out for four weeks by feeding (free feeding) respectively the concentrate feeds with the respective composition described under to the groups. The results were as follows: two bullocks of the control group showed intermitten excessive distensions of their abdomens, namely, the two bullocks were affected with a slight bloat; all the bullocks of the test group did not show bloat at all.

| Compositions of given concentrate feeds (parts by weight) | | |
|---|---|---|
| | Basic feed (Note 1) | Agent for bloat-prevention or -treatment of the present invention (Note 2) |
| Test group | 100 | 0.5 |
| Control group | 100 | 0 |

Note 1.
DCP (digestible crude protein): 9.3%
TDN (total amount of digestible nutrients): 76%
Note 2.
The same crude products as used in examples 11-18 was used.

EXAMPLE 20

Twenty five g of the same crude products as used in examples 11-19 was diluted with water and the resulted 1/10 crude products solution was compulsorily administered perorally into one bullock (Holstein bullock weighing about 500 kg, fed by the system feeding much concentrate feed) being ill from a chronic serious bloat and the change with the passage of time in relation to his girth was examined. The results are shown below. One hour after the administration, a thorough vanishment of the distension of his abdomen showed the return of healthy state.

| Time after the administration (hour) | Girth (cm) |
|---|---|
| 0 | 260 |
| 0.5 | 241 |
| 1.0 | 230 |

EXAMPLE 21

Fifty g of the same crude products as used in examples 11-20 was diluted with water and the resulted 1/10 crude products solution was compulsorily administered perorally into one bullock (Japanese indegenous black-haired bullock, the weight: about 500 kg) being ill from a chronic serious bloat and the change with the passage of time in relation to his girth was examined. The results clearly showed the treating effect on the bloat as follows:

| Time after the administration (hour) | Girth (cm) |
|---|---|
| 0 | 235 |
| 1.0 | 217 |

EXAMPLE 22

The test was carried out as follows: Into one Japanese indegenous brown-haired bullock (the weight: about 650 kg) equipped with a fistula was fed the feed (1) (the same bloat-inducing feed as used in examples 15-17, comprising 61% barley, 22% alfalfa meal, 16% soybean cake and 1% NaCl) at the rate of 8 kg/day for two weeks and thereafter consequtively fed the feed (2) (the feed prepared by adding the same crude products as used in examples 11-21 into the feed (1) in an amount of 1%) at the rate of 8 kg/day as in the case of the feed (1). The rumen juice was collected 4, 8, 11 and 14 days after the start of each feeding during the feedings of the feeds (1) and (2) to measure viscosities and Stable IVIs. The observations were also done. The results were shown in Table 4. The results showed that mixture of the present invention has a preventive effect on bloat.

TABLE 4

| Feed given | Feeding period | State of the rumen juice (Note 1) Viscosity (cp) | | Stable IVI (%) | Observation |
| --- | --- | --- | --- | --- | --- |
| | | Before the filtration (Note 2) | After the filtration (Note 3) | | |
| Feed (1) (only the bloat-inducing feed) | 2 weeks | 12.1 | 6.2 | 6.0 | The fistula was separated three times owing to the rise in the internal pressure of the rumen, during the feeding period. |
| Feed (2) (the bloat-inducing feed + the crude products of the present invention (%)) | " | 7.8 | 3.9 | 0 | No abnormality |

Note 1. The average value of four times (4, 8, 11 and 14 days after)
Note 2. The measurements were carried out before the filtration with double gauzes.
Note 3. The measurements were carried out after the elimination of the admixtures with double gauzes.

What is claimed is:

1. An agent for bloat-prevention or -treatment comprising at least saccharide fatty acid ester and fatty acid salt in the weight ratio in the range of 90:10 to 10:90, wherein the saccharide fatty acid ester and fatty acid salt are diluted with at least one member selected from the group consisting of water, cereal grains, chaff and bran, oil seed mean, and oil or fat.

2. An agent for bloat-prevention or -treatment as claimed in claim 1, wherein the saccharide fatty acid ester is sucrose fatty acid ester.

3. An agent for bloat-prevention or -treatment as claimed in claim 1, wherein the saccharide fatty acid ester is raffinose fatty acid ester.

4. An agent for bloat-prevention or -treatment as claimed in claim 1, wherein the saccharide fatty acid ester is maltotriose fatty acid ester.

5. An agent for bloat-prevention or -treatment as claimed in claim 1, wherein the fatty acid salt is fatty acid alkali metal salt.

6. An agent for bloat-prevention or -treatment as claim in claim 1, wherein the fatty acid salt is fatty acid basic amino acid salt.

7. A method for preventing or treating bloat in ruminants mammals, comprising feeding to said ruminant mammals an amount sufficient for bloat-prevention or bloat-treatment of a mixture of 3–97% saccharide fatty acid ester and 97–3% fatty acid salt.

8. A method according to claim 7, wherein said ruminant mammals are selected from the group consisting of cattle, sheep and goats.

9. A method according to claim 7, wherein said mixture comprises 95–5% of said saccharide fatty acid ester and 95–5% of said fatty acid salt.

10. A method according to claim 7, wherein said mixture comprises 90–10% of said saccharide fatty acid ester and 10–90% of said fatty acid salt.

11. A method according to claim 7, wherein said mixture is diluted with at least one member selected from the group consisting of water, cereal grains, chaff and bran, oil seed meal, and oil or fat.

12. A method according to claim 7, wherein said mixture is added to drinking water or feed in an amount of 0.005–10% by weight.

13. An animal feed or drinking water composition comprising 0.02–3% by weight of a mixture of 90–10% of a saccharide fatty acid ester and 10–90% of a fatty acid salt, the balance of said composition being water for drinking or feed.

* * * * *